(12) United States Patent
Zhang et al.

(10) Patent No.: US 7,736,669 B2
(45) Date of Patent: Jun. 15, 2010

(54) POROUS STRUCTURES, AND METHODS OF USE

(75) Inventors: Miqin Zhang, Bothell, WA (US); Zhensheng Li, Seattle, WA (US)

(73) Assignee: University of Washington, Seattle, WA (US)

( * ) Notice: Subject to any disclaimer, the term of this patent is extended or adjusted under 35 U.S.C. 154(b) by 1373 days.

(21) Appl. No.: 11/002,996

(22) Filed: Nov. 30, 2004

(65) Prior Publication Data
US 2006/0115511 A1    Jun. 1, 2006

(51) Int. Cl.
*A61K 9/00* (2006.01)
(52) U.S. Cl. .................. 424/488; 424/423; 424/413; 424/426; 424/400
(58) Field of Classification Search .................. 424/501
See application file for complete search history.

(56) References Cited

U.S. PATENT DOCUMENTS

| | | | |
|---|---|---|---|
| 5,830,493 A | | 11/1998 | Yokota et al. |
| 5,836,970 A | * | 11/1998 | Pandit .................. 606/213 |
| 5,888,987 A | * | 3/1999 | Haynes et al. .................. 514/54 |
| 6,027,744 A | * | 2/2000 | Vacanti et al. .................. 424/426 |
| 6,150,581 A | * | 11/2000 | Jiang et al. .................. 602/50 |
| 6,171,340 B1 | * | 1/2001 | McDowell .................. 623/18.11 |
| 6,207,218 B1 | * | 3/2001 | Layrolle et al. .................. 427/2.27 |
| 6,699,848 B1 | * | 3/2004 | Barbeau .................. 514/54 |
| 6,836,970 B2 | * | 1/2005 | Hirano .................. 33/203 |
| 2005/0118230 A1 | * | 6/2005 | Hill et al. .................. 424/426 |

OTHER PUBLICATIONS

Lai et al. The preparation and characterization of drug loaded alginate and chitosan sponges, Aug. 28, 2002, Internation Journal of Pharmaceutics.*
Lai et al., The preparation and characterization of drug loaed alginate and chitosan sponges), of record.*
Chu, T.M., et al., "Mechanical and in vivo performance of hydroxyapatite Implants With Controlled Architectures," *Biomaterials* 23:1283-1293, 2002.
Chung, T.W., et al., "Preparation of Alginate/Galactosylated Chitosan Scaffold for Hepatocyte Attachment," *Biomaterials* 23:2827-2834, Jul. 2002.
Coppi, G., et al., "Chitosan-Alginate Microparticles as a Protein Carrier," *Drug Dev. Ind. Pharm.* 27(5):393-400, 2001.
Dillon, G.P., "The Influence of Physical Structure and Charge on Neurite Extension in a 3D Hydrogel Scaffold," *J. Biomater. Sci. Polymer Edn* 9(10):1049-1069, 1998.
Dornish, M., et al., "Standards and Guidelines for Biopolymers in Tissue-Engineered Medical Products: ASTM Alginate and Chitosan Standard Guides," *Ann. New York Acad. Sci.*, 2001, pp. 388-397.

(Continued)

*Primary Examiner*—Robert A Wax
*Assistant Examiner*—Melissa S Mercier
(74) *Attorney, Agent, or Firm*—Christensen O'Connor Johnson Kindness PLLC

(57) ABSTRACT

The present invention provides porous structures that each comprise chitosan, alginate and divalent metal cations, wherein: (a) the chitosan is ionically linked to the alginate; and (b) the structure is porous and has a compressive yield strength of at least 0.35 MPa. The present invention also provides methods for making the porous structures, and methods for using the porous structures as substrates to grow living cells.

10 Claims, 2 Drawing Sheets

OTHER PUBLICATIONS

Gåserød, O., et al., "Microcapsules of Alginate-Chitosan. II. A Study of Capsule Stability and Permeability," *Biomaterials* 20:773-783, Apr. 1999.

Gutowska, A., et al., "Injectable Gels for Tissue Engineering," *Anat. Rec.* 263:342-349, 2001.

Hari, P.R., et al., "Chitosan/Calcium-Alginate Beads for Oral Delivery of Insulin," *J. Appl. Polymer Sci.* 59:1795-1801, 1996.

Hutmacher, D.W., et al., "An Introduction to Biodegradable Materials for Tissue Engineering Applications," *Ann. Acad. Med. Singapore* 30(2):183-191, 2001.

Kim, H.J., "Polyelectrolyte Complex Composed of Chitosan and Sodium Alginate for Wound Dressing Application," *J. Biomater. Sci. Polymer Edn* 10(5):543-556, 1999.

Lauffenburger, D.A., and D.V. Schaffer, "The Matrix Delivers: Gene Therapy and Tissue Engineering Team Up to Speed Bone Regeneration," *Nat Med.* 5(7):733-734, 1999.

Li, J., et al., "Culture of Primary Rat Hepatocytes Within Porous Chitosan Scaffolds," *J. Biomed. Mat. Res.* 67A(3):938-943, Dec. 1, 2003.

Liu, L.-S., et al., "Controlled Release of Interleukin 2 for Tumor Immunotherapy Using Alginate/Chitosan Porous Microspheres," *J. Controlled Release* 43:65-74, Jan. 1997.

Muzzarelli, R.A., et al., "Stimulatory Effect on Bone Formation Exerted by a Modified Chitosan," *Biomaterials* 15:1075-1081, 1994.

Overgaard, S., et al., "Immobilization of Hybridoma Cells in Chitosan Alginate Beads," *Can. J. Chem. Eng.* 69(2):439-443, Apr. 1991.

Savant, V.D., and J.A. Torres, "Protein Adsorption on Chitosan-Polyanion Complexes: Application to Aqueous Food Processing Wastes," in H. Chen and C. Weller (eds.), *Structure and Functionality of Biopolymers*, 2001, pp. 537-542.

Shanmugasundaram, N., et al., "Collagen-Chitosan Polymeric Scaffolds for the in vitro Culture of Human Epidermoid Carcinoma Cells," *Biomaterials* 22:1943-1951, 2001.

Sugimoto, M., et al., "Preparation and Characterization of Water-Soluble Chitin and Chitosan Derivatives," *Carbohydrate Polymers* 3649-59, 1998.

Suh, J.K., and H.W. Matthew, "Application of Chitosan-Based Polysaccharide Biomaterials in Cartilage Tissue Engineering: A Review," *Biomaerials* 21:2589-2598, 2000.

Takahashi, K.T., et al., "Characteristics of Polyion Complexes of Chitosan With Sodium Alginate and Sodium Polyacrylate," *Int. J. Pharm.* 61:35-41, 1990.

Thomson, R.C., et al., "Fabrication of Biodegradable Polymer Scaffolds to Engineer Trabecular Bone," *J. Biomater. Sci. Polym. Edn.* 7(1):23-38, 1995.

Wake, M.C., et al., "Pore Morphology Effects on the Fibrovascular Tissue Growth in Porous Polymer Substrates," *Cell Transplant* 3(4):339-343, 1994.

Wang., L., et al., "Chitosan-Alginate-$CaCl_2$ System for Membrane Coat Application," *J. Pharm. Sci.* 90(8):1134-1142, Aug. 2001.

Whang, K., et al., "Engineering Bone Regeneration With Bioabsorbable Scaffolds With Novel Microarchitecture," *Tissue Eng.* 5(1):35-51, 1999.

Yang, S., et al., "The Design of Scaffolds for Use in Tissue Engineering. Part I. Traditional Factors," *Tissue Eng.* 7(6):679-689, 2001.

Zhang, Y., and M. Zhang, "Calcium Phosphate/Chitosan Composite Scaffolds for Controlled in vitro Antibiotic Drug Release," *J. Biomed. Mater. Res.* 62:378-386, 2002.

Zhang, Y., and M., Zhang, "Synthesis and Characterization of Macroporous Chitosan/Calcium Phosphate Composite Scaffolds for tissue Engineering," *J. Biomed. Mater. Res.* 55:304-312, 2001.

Zhang, Z., et al., "Pore Size, Tissue Ingrowth, and Endothelialization of Small-Diameter Microporous Polyurethane Vascular Prosthesis," *Biomaterials* 25:177-187, 2004.

\* cited by examiner

POROUS STRUCTURES, AND METHODS OF USE

STATEMENT OF GOVERNMENT LICENSE RIGHTS

The U.S. Government has a paid-up license in this invention and the right in limited circumstances to require the patent owner to license others on reasonable terms as provided for by the terms of grant NSF-EEC 9529161 awarded by the National Science Foundation.

FIELD OF THE INVENTION

The present invention relates to porous structures used as substrates for the growth of living cells in vivo or in vitro.

BACKGROUND OF THE INVENTION

In bone tissue engineering a biodegradable scaffold serves as a temporary substrate, inserted into the sites of defective or lost bone, to support and stimulate bone tissue regeneration. The scaffold gradually degrades and is replaced by new bone tissue (Persidis, A., *Nat. Biotechnol.* 17:508-10, 1999; Service, R. F., *Science* 289:1498-1500, 2000; Petite, H., et al., *Nat. Biotechnol.* 18:959-63, 2000). Ceramics and polymers, referred to as bioceramics and biopolymers, respectively, have been developed for use as tissue engineering scaffolds. Bioceramics have a chemical composition resembling that of natural bone, and allow the growth of bone (a process called osteogenesis) to occur (Jarcho, M., *Clin. Orthop.*, 259-78, 1981; Hench, L. L. and Wilson, J., *Science* 226:630-6, 1984).

Despite their favorable biological properties, bioceramics are inherently brittle and have low biodegradation rates, which severely limits their clinical use. Biopolymers, on the other hand, have some distinct advantages over ceramic materials. Their biodegradation rates and mechanical properties can be tailored to a certain extent for specific applications. They are particularly amenable for implantation and can be easily manufactured into desired shapes (Yang, S., et al., *Tissue Eng.* 7:679-89, 2001; Niklason, L. E., *Nat. Biotechnol.* 18:929-30, 2000). The major concern associated with polymer scaffolds is low mechanical strength and inability to retain their shape.

A number of natural and synthetic polymers have been studied for use as scaffolds. The typical synthetic polymers include poly(glycolic acid) (PGA), poly(L-lactic acid) (PLLA) (Saito, N., et al., *Nat. Biotechnol.* 19:332-5, 2001; Chen, G., et al., *J. Biomed. Mater. Res.* 57:8-14, 2001; Andriano, K. P., et al., *J. Biomed. Mater. Res.* 48:602-12, 1999) and their copolymer, for example, poly(DL-lactic-co-glycolic acid) (PLGA) (Yang, S., et al., *Tissue Eng.* 7:679-89, 2001). These synthetic polymers demonstrate insufficient cell adhesion, however, and their surfaces are hydrophobic, hindering cell growth in a three-dimensional architecture (Chen, G., et al., *J. Biomed. Mater. Res.* 51:273-9, 2000; Lahiji, A., et al., *J. Biomed. Mater. Res.* 51:586-95, 2000). They also lack functional groups available for further surface modifications (Thomson, R. C., et al., *J. Biomater. Sci. Polym. Ed.* 7:23-38, 1995). When implanted in vivo, at least some synthetic biopolymers release acidic degradation products and invoke a chronic immune reaction that is harmful to host tissues (Daniels, A. U., et al., *J. Appl. Biomater.* 5:51-64, 1994). In addition, certain bulk hydrolyzing PLGA copolymers have been shown to significantly reduce osteogenesis in healing bone (Martin, C., et al., *Biomaterials* 17:2373-80, 1996).

Chitosan, a natural cationic polymer, is biologically renewable, biodegradable, biocompatible, non-antigenic, and non-toxic. Chitosan structures have a hydrophilic surface that promotes cell adhesion, proliferation and differentiation, and evokes a minimal foreign body reaction on implantation (Suh, J. K. and Matthew, H. W., *Biomaterials* 21:2589-98, 2000; Hutmacher, D. W., et al., *Ann. Acad. Med. Singapore* 30:183-91, 2001). Chitosan scaffolds promote the growth of bone cells within the scaffolds, and can enhance bone formation both in vitro and in vivo (Muzzarelli, R. A., et al., *Biomaterials* 15:1075-81, 1994). In spite of its general acceptance as a material that is compatible with living tissue, chitosan is mechanically weak and unstable, and unable to maintain a predefined shape for transplantation as a result of swelling (Shanmugasundaram, N., et al., *Biomaterials* 22:1943-51, 2001). Alginate, an anionic polymer, widely used as an instant gel for bone tissue engineering (Lauffenburger, D. A. and Schaffer, D. V., *Nat. Med.* 5:733-4, 1999), is biocompatible, hydrophilic, and biodegradable under normal physiological conditions (Gutowska, A., et al., *Anat. Rec.* 263:342-9, 2001).

The present invention provides biodegradable porous structures made from chitosan and alginate. The compressive strength of the structures, and other physical properties, such as their elasticity, ability to retain their shape, and ability to promote the growth of bone-forming cells, facilitate the use of the structures as substrates to support the growth of bone in vivo or in vitro. Additionally, the porous structures of the invention can also be used as substrates for the growth of cells that form cartilage.

SUMMARY OF THE INVENTION

In one aspect, the present invention provides porous structures comprising chitosan, alginate and divalent metal cations, wherein, with respect to each structure of the invention: (a) the chitosan is ionically linked to the alginate; and (b) the structure is porous and has a compressive yield strength of at least 0.35 MPa. The porous structures are typically composed mainly of chitosan molecules that are ionically linked to alginate molecules, and also include divalent metal cations that are ionically linked to the alginate molecules, thereby enhancing the mechanical strength of the structures. Other molecules (e.g., biologically active molecules) can be included in the porous structures of the invention. The porous structures of the present invention can be used, for example, to grow bone-forming cells and/or cartilage-forming cells either in vivo or in vitro.

In another aspect, the present invention provides methods for making porous structures comprising chitosan, alginate and divalent metal cations, wherein the methods each comprise the steps of: (a) freezing a solution comprising chitosan and alginate to produce a frozen structure; (b) drying the frozen structure to produce a dried structure; and (c) contacting the dried structure with divalent metal cations to produce a porous structure wherein the chitosan is ionically linked to the alginate, and the divalent metal cations are ionically linked to the alginate. The methods of this aspect of the invention can be used, for example, to make the porous structures of the present invention.

In a further aspect, the present invention provides methods for growing living cells in a porous structure. The methods of this aspect of the invention each include the step of growing living cells in pores defined by a porous structure comprising chitosan, alginate and divalent metal cations, wherein (a) the porous structure comprises chitosan that is ionically linked to alginate; and (b) the structure has a compressive yield strength of at least 0.35 MPa. Any of the porous structures of the present invention can be used in the practice of the methods of the present invention for growing living cells. Examples of living cells that can be grown in the porous structures include bone-forming cells (called osteoblasts)) and/or cartilage-forming cells (called chondrocytes).

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
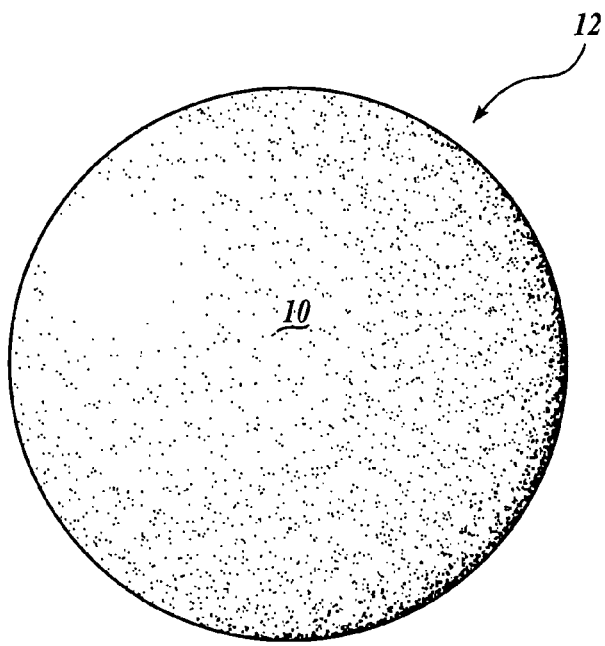
FIG. 1 is a drawing of a spherical, porous, structure of the present invention.

In one aspect, the present invention provides porous structures that each include chitosan, alginate and divalent metal cations, wherein: (a) the chitosan is ionically linked to the alginate; and (b) the structure has a compressive yield strength of at least 0.35 MPa. Porous structures of the present invention can be biodegradable or non-biodegradable, although typically the porous structures of the present invention are biodegradable.

The porous structures include chitosan that is ionically linked to alginate. As used herein, the term "ionically linked" refers to a non-covalent chemical bond between two ions having opposite electrical charges (e.g., between an amine group present on chitosan and a carboxyl group present on alginate).

In addition to the ionic linkages between chitosan and alginate, ionic linkages are also present between divalent metal ions (e.g., $Ca^{2+}$, $Ba^{2+}$, $Mg^{2+}$, or $Sr^{2+}$) and alginate molecules present in the porous structures of the present invention (e.g., between divalent metal ions and carboxyl groups on alginate molecules). These ionic linkages further strengthen the porous structures of the present invention.

Thus, the mechanical strength of the porous structures of the present invention mainly depends on ionic linkages between chitosan and alginate, and between divalent metal cations and alginate. Typically, chitosan molecules are not covalently linked to alginate molecules in the porous structures of the present invention (although a low level of covalent linkages may be present between the chitosan molecules and alginate molecules in the porous structures of the present invention).

Chitosan useful for making the porous structures of the present invention typically has an average molecular weight in the range of from 200 kiloDaltons to 1000 kiloDaltons (kiloDaltons is abbreviated as kDa). In general, porous structures of the present invention made from higher molecular weight chitosan have greater mechanical strength than porous structures of the present invention made from lower molecular weight chitosan. An exemplary range of percentage deacetylation of chitosan useful for making the porous structures of the present invention is from 80% to 100% deacetylation.

Alginates are a group of polysaccharides made by certain seaweeds (collectively referred to as brown seaweeds), and are linear polysaccharides of β-D-mannuronic acid and α-L-guluronic acid. Alginate salts (e.g., sodium alginate) are typically used in the practice of the present invention. While not wishing to be bound by theory, it is believed that the divalent metal cations form ionic linkages between adjacent alginate chains, thereby ionically cross-linking adjacent alginate molecules. In particular, it is believed that the divalent metal cations form stronger ionic linkages with the guluronic acid residues of adjacent alginate molecules than with the mannuronic acid molecules. Thus, alginates that include a higher proportion of guluronic acid are preferred for making porous structures of the present invention.

The ratio of chitosan to alginate in the porous structures of the present invention is typically in the range of from 1:1 to 4:1, such as from 1:1 to 3:1, or such as from 1:1 to 2:1.

The porous structures of the present invention typically, although not necessarily, consist almost entirely of chitosan and alginate. For example, chitosan and alginate may together constitute more than 90% by weight, or more than 95% by weight, or more than 97% by weight, or more than 99% by weight, or more than 99.5% by weight, or more than 99.9% by weight, of a porous structure of the present invention. Smaller amounts of other components may also be present in the porous structure. For example, divalent metal ions are present in a porous structure, typically in an amount less than 1% by weight of the porous structure. Small amounts of biologically active molecules such as proteins, growth factors, and hydroxyl apatite can also be incorporated to promote bone growth into a porous structure. Typically, each of these components, when present, are present in an amount of less than 1% by weight, such as less than 0.1% by weight, or such as less than 0.01% by weight of the porous structure.

The porous structures of the present invention each have a compressive yield strength of at least 0.35 MPa (Mega Pascal). Some porous structures of the present invention have a compressive yield strength in the range of from 0.35 MPa to 0.5 MPa. Thus, for example, a porous structure can have a compressive yield strength having any value that falls between 0.35 MPa and 0.5 MPa. Some porous structures of the present invention have a compressive yield strength in the range of from 0.4 MPa to 0.5 MPa. Thus, for example, a porous structure can have a compressive yield strength having any value that falls between 0.4 MPa and 0.5 MPa. A method for measuring the compressive yield strength of the porous structures of the invention is set forth in Example 2 herein.

Some porous structures of the present invention have a compressive modulus in the range of from 5 MPa to 8 MPa, such as from 5 MPa to 7 MPa, or such as from 6 MPa to 8 MPa. Thus, for example, a porous structure can have a compressive modulus having any value that falls between 5 MPa and 8 MPa.

Some porous structures of the present invention have a porosity in the range of from 88% to 96% (e.g., a porosity in the range of from 88% to 95%, or a porosity in the range of from 88% to 94%). Thus, for example, a porous structure can have a porosity having any value that falls between 88% and 96%. These embodiments of the porous structures of the present invention therefore combine a highly porous structure with a substantial compressive yield strength. Thus, some porous structures of the present invention have a compressive yield strength in the range of from 0.35 MPa to 0.5 MPa, a compressive modulus in the range of from 5 MPa to 8 MPa, and a porosity in the range of from 88% to 96%. A method for measuring the porosity of porous structures of the present invention is set forth in Example 3 herein.

One or more types of biologically active molecules can be included in the porous structures of the present invention (e.g., included in the solution of chitosan and alginate used to make the porous structures). In this regard, the porous structures of the present invention can be prepared from a solution of chitosan and alginate that has a pH that is acidic, basic or neutral. Thus, if a biologically active molecule is added to the solution of chitosan and alginate, the pH of the solution can be adjusted to a value that promotes the physical and functional stability of the biologically active molecule. In contrast, porous structures made entirely from chitosan can only be fabricated from an acidic chitosan solution (an acidic pH being required to dissolve the chitosan).

Examples of biologically active molecules that can be incorporated into the porous structures of the present invention include antibiotics (e.g., gentamycin sulfate), and proteins, such as growth factors that promote bone growth and/or cartilage growth (e.g., transforming growth factor-β1).

Figure 2:
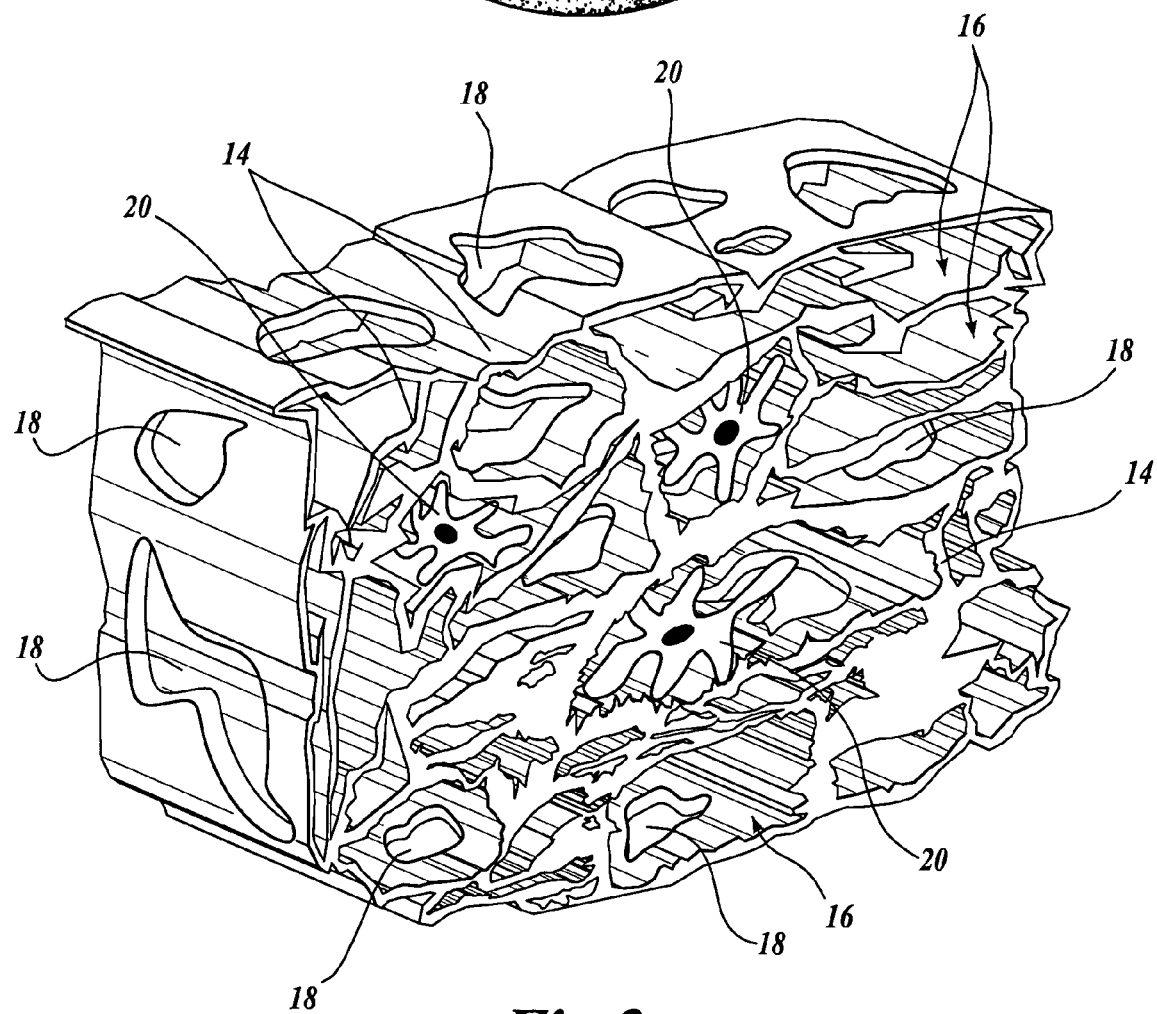
FIG. 2 is a drawing of a magnified portion of the spherical, porous, structure of FIG. 1.

FIG. 1 shows a drawing of a representative porous structure 10 of the present invention. Porous structure 10 is spherical and includes a body 12. FIG. 2 shows a drawing of a magnified portion of the spherical, porous, structure of FIG. 1. As shown more clearly in FIG. 2, body 12 is composed of numerous, linked, pore walls 14 that define numerous pores 16. All, or substantially all, of pores 16 are connected to at least one other pore 16. For example, holes 18 in pore walls 14 connect at least some pores 16. Thus, pores 16 form an interconnected network of pores 16 within structure body 12. Representative porous structure 10 includes living cells 20 within pores 16.

Although the specific embodiment of porous structure 10 shown in FIG. 1 is spherical, porous structure 10 can be made in any shape (e.g., regular geometrical shapes or irregular shapes). Thus, for example, porous structure 10 can be hemispherical, cylindrical, rectangular, cubic, or pyramidal. Porous structures 10 can be any desired size.

Pores 16 can have any desired diameter. The diameter of pores 16 is typically expressed as an average diameter value. A method for measuring average diameter of pores 16 is set forth in Example 4 herein. Representative values for the average diameter of pores 16, in porous structures 10 useful as supports for growing bone cells or cartilage cells, are from about 50 μm to about 200 μm, such as from about 100 μm to about 200 μm, wherein μm is the abbreviation for micrometer.

The porous structures of the present invention are useful, for example, as substrates for growing living cells in vivo or in vitro. Thus, for example, the porous structures of the present invention can be used to grow bone cells which produce bone. The bone grows in and/or around the porous structure, depending, at least in part, on the location of the bone-producing cells on and/or within the porous structure. Bone grown in vitro can be implanted into a living body where required. For example, the bone can be implanted into a living body (e.g., mammalian body, such as a human body) to repair damaged bone (e.g., bone damaged by physical trauma) or to replace missing bone (e.g., bone removed during surgery to remove bone cancer). The implanted porous structure is degraded by the living body into which it is implanted, leaving the bone at the site of implantation. Similarly, a porous structure of the invention can be seeded with bone-forming cells and implanted into a living body. The cells produce bone over time, and the porous structure is gradually degraded by the living body. Again by way of example, the porous structures of the present invention can be used, in vivo or in vitro, to grow cartilage cells which produce cartilage which may be used to replace missing or damaged cartilage in a mammalian body (e.g., in a joint, such as a knee joint).

In another aspect the present invention provides methods for making porous structures which are useful, for example, as substrates for growing bone and/or cartilage. The methods of this aspect of the invention can be used, for example, to make the porous structures of the present invention. The methods of this aspect of the invention include the steps of: (a) freezing a solution comprising chitosan and alginate to produce a frozen structure; (b) drying the frozen structure to produce a dried structure; and (c) contacting the dried structure with divalent metal cations to produce a porous structure wherein the chitosan is ionically linked to the alginate, and the divalent metal cations are ionically linked to the alginate.

The ratio of chitosan to alginate in the solution is typically in the range of from 1:1 to 4:1. The concentration of alginate in the solution is typically in the range of from 1.5% (w/v) to 2.5% (w/v), such as from 1.5% (w/v) to 2.0% (w/v), or such as from 2.0% (w/v) to 2.5% (w/v). The concentration of chitosan in the solution is typically in the range of from 1.5% (w/v) to 2.5% (w/v), such as from 1.5% (w/v) to 2.0% (w/v), or such as from 2.0% (w/v) to 2.5% (w/v). Thus, for example, the solution can contain any combination of concentrations of alginate (from 1.5% (w/v) to 2.5% (w/v)) and chitosan (from 1.5% (w/v) to 2.5% (w/v)).

The pH of the solution of chitosan and alginate is typically from 6.0 to 8.0. The solution of chitosan and alginate is typically frozen at a temperature of from −10° C. to −20° C. The frozen structure is dried, for example by lyophilization. The moisture content of the dried structure may closely approach zero (e.g., a moisture content of less than 0.5% by weight, such as less than 0.1% by weight, such as less than 0.05% by weight).

The dried structure is contacted with divalent metal cations that form ionic linkages with the alginate and/or chitosan, thereby imparting mechanical stability to the structure. Examples of useful divalent metal cations are $Ca^{2+}$, $Ba^{2+}$, $Mg^{2+}$, and $Sr^{2+}$ ions. For example, the dried structure can be immersed in a solution of divalent metal cations, or, for example, can be sprayed with a solution of divalent metal cations. A useful, exemplary, concentration of divalent metal cations in a solution of divalent metal cations is about 1% w/v.

While not wishing to be bound by theory, it is believed that the divalent metal cations mainly form ionic linkages between adjacent alginate chains, thereby ionically cross-linking the adjacent alginate chains. In particular, it is believed that the ionic linkages are mainly formed between the metal ions and guluronic acid residues of adjacent alginate chains.

The freezing temperature affects the porosity, pore size, and pore distribution in the porous structures. In general, porous structures prepared at lower freezing temperatures exhibit smaller pores with a more uniform pore structure. In general, porous structures prepared at higher freezing temperature have larger pores than porous structures prepared at lower freezing temperature, and the shapes of the pores are heterogeneous.

The molecular weights of the chitosan and alginate also affect pore size and structure. Typically, use of higher molecular weight chitosan and alginate produces porous structures having smaller pores that are less interconnected compared to porous structures produced using lower molecular weight chitosan and alginate.

The shape of the porous structure can be controlled, for example, by freezing the solution of chitosan and alginate in a mold having a desired shape. For example, a rectangular porous structure can be made by freezing the solution of chitosan and alginate in a mold defining a rectangular space.

In another aspect, the present invention provides porous structures made by a method of the present invention for making porous structures. Thus, in one aspect, the present invention provides porous structures comprising chitosan, alginate, and divalent metal cations wherein: (a) the chitosan is ionically linked to the alginate; (b) the structure is porous and has a compressive yield strength of at least 0.35 MPa; (c) the porous structures are made by a process comprising the steps of (1) freezing a solution comprising chitosan and alginate to produce a frozen structure; (2) drying the frozen structure to produce a dried structure; and (3) contacting the dried structure with divalent metal cations to produce a porous structure wherein the chitosan is ionically linked to the alginate, and the divalent metal cations are ionically linked to the alginate.

The porous structures of the present invention are useful, for example, as substrates for growing living cells in vivo or in vitro. Thus, in another aspect, the present invention provides methods for growing living cells in a porous structure. The methods each comprise the step of growing living cells in pores defined by a porous structure comprising chitosan, alginate and divalent metal cations, wherein (a) the chitosan is ionically linked to alginate; and (b) the structure has a compressive yield strength of at least 0.35 MPa. Any of the porous structures of the present invention are useful in the practice of the methods for growing living cells in a porous structure. Examples of living cells that can be grown in the porous structures of the invention include bone-forming cells, and cartilage-forming cells.

By way of example, bone-forming cells can be grown in a porous structure of the present invention by first soaking the porous structure with simulated body solution and then immersing the structure in Dulbecco's modified eagle medium (D-MEM) containing osteoblast-like MG63 cells (ATCC accession number ATCC CRL-1427). The structure is immersed in the D-MEM medium for a period of time sufficient to permit the cells to grow on and within the porous structure. Again by way of example, cartilage-forming cells can be grown in a porous structure of the present invention by immersing the porous structure in D-MEM cell culture medium containing chondrocytes (e.g., ATCC accession number ATCC HTB-94) for a period of time sufficient to permit the cells to grow on and within the porous structure.

The following examples merely illustrate the best mode now contemplated for practicing the invention, but should not be construed to limit the invention.

EXAMPLE 1

This Example describes the preparation and some physical properties of representative porous structures of the present invention. The porous structures were scaffolds useful as substrates for growing bone cells.

Preparation of porous chitosan-alginate and pure chitosan scaffolds: Chitosan (Mol. Wt. 400,000, 85% deacetylated) and sodium alginate powders (Cat # 180947 MFCD00081310, Sigma-Aldrich) were used as received. 4.8 grams of sodium alginate were dissolved in 120 ml 1N NaOH, and 4.8 grams of chitosan were dissolved in 80 ml 1N acetic acid. The two solutions were mixed under constant stirring in a blender for one hour to obtain a homogeneous 4.8% w/v (2.4% chitosan and 2.4% alginates) chitosan-alginate solution. The pH of the chitosan-alginate solution was adjusted to pH 7.4 by adding 2N acetic acid dropwise. The solution was introduced into 24-well cell culture plates and maintained in a freezer at −10° C. for 24 hours. The samples were then lyophilized in a freeze dryer until dried. The dried scaffolds were cross-linked with 1% w/v $CaCl_2$ solution for 10-15 min. The scaffolds were washed with DI water twice and immersed in DI water overnight to remove unbound $CaCl_2$. The samples were then dried in a freeze dryer. Pure chitosan scaffolds (as a control) were prepared following the procedure reported previously (Whang, K., et al., *Tissue Eng.* 5:35-51, 1999; Wake, M. C., et al., *Cell Transplant* 3:339-43, 1994). All the samples were kept dry in air for sterilization.

Mechanical testing: The compressive yield strength and compressive modulus of scaffolds were tested using an Instron 4505 mechanical tester with 10 Kilo Newton load cells following the guidelines in ASTM D5024-95a (Whang, K., et al., *Tissue Eng.* 5:35-51, 1999). The specimens were circular discs of 13 mm in diameter and 12 mm in thickness. The crosshead speed of the Instron tester was set at 0.4 mm/min and load was applied until the specimens were compressed to approximately 30% of their original thickness.

Polarized Fourier Transformed Infrared Spectroscopy: Infrared Spectroscopy was used to characterize powdered chitosan-alginate scaffold before and after coacervation. A dried sample of 2 mg powder was carefully mixed with 300 mg dry KBr and pressed into a pellet using a macro KBr die kit. The solid pellet was placed in a magnetic holder. Polarized Fourier Transformed Infrared (FTIR) spectra of 2000 scans at 8 $cm^{-1}$ were obtained using a Nicolet 5DX spectrometer with a DTGS detector. The sample compartment of the FTIR machine was purged with dry air for one hour to remove moisture before characterization.

Swelling behavior: The swelling behavior of the scaffolds prepared as described herein was investigated by exposing them to the following media of different pH: 1N HCl, 1N NaOH, and phosphate buffered saline (PBS) solutions. The specimens were cylindrical in shape with a diameter of 13 mm and a thickness of 3 mm. The swelling behavior was quantified by measuring the changes in sample diameter as a function of sample immersion time in the media. Three specimens were measured for each sample.

Cell Culture and Imaging: To study cell adhesion, proliferation and osteoconductivity, chitosan and chitosan-alginate scaffolds were seeded with MG63 osteoblast cells (American Type Culture Collection, ATCC accession number CRL-1427) and cultured in standard culture medium without reagents that promote osteogenesis. The specimens were discs with a diameter of 13 mm, a thickness of 3 mm and a small hole in the center. Osteoblast-like MG63 cell lines isolated from human osteosarcoma were selected because they express a number of characteristic features of osteoblasts (Porter, B. D., et al., *J. Biomech. Eng.* 122:286-8, 2000). The scaffold discs were sterilized with ethylene oxide gas and placed in a 12-well cell culture plate. Approximately $5 \times 10^5$ osteoblast-like MG63 cells in 1 ml Dulbecco's Modified Eagle Medium (D-MEM) (Invitrogen Life Technologies) were seeded on the scaffold discs. The medium contained 10% fetal bovine serum (FBS), 50 $IU.ml^{-1}$ penicillin, and 50 $\mu g.ml^{-1}$ streptomycin. The samples were then placed in an incubator for 30 minutes and transferred to another cell culture plate. The medium was changed after 24 hours for the first time, and once every three days thereafter. The morphology of the cells cultured on the scaffolds was examined by using a model JEOL, JSM-840A, scanning electron microscope (SEM). For SEM observation, scaffolds were fixed with Karnovsky's Fixative over night at room temperature and dehydrated in 50%, 75%, 95%, 100% ethanol, successively, for 2 hours. The samples were then air-dried under vacuum, coated with Au/Pd, and examined with a scanning electron microscope (SEM).

Von Kossa stain: Scaffolds were fixed with 4% paraformaldehyde overnight, then dehydrated and embedded with paraffin. The scaffolds were cut into slices of 5 μm in thickness. Samples were stained in 5% $AgNO_3$ solution under light for 60 min and developed in 1% Kodak film developer D-76 for 2 minutes, followed by fixation in a 5% solution of sodium thiosulfate for 5 min, and counterstaining with Nuclear Fast Red for 5 min.

Cell proliferation and viability: Cell proliferation was assessed using the colorimetric indicator Alamar Blue assay (Alamar BioSciences, Sacramento, Calif.). Alamar Blue changes color by chemical reduction of the membrane potential across a cell. Scaffolds were seeded with cells in DMEM cell culture medium. After 24 hours of cell seeding, the scaffolds were washed with PBS and placed into fresh, sterile 12-well culture plates. 2 ml of DMEM containing 1% v/v FBS and 10% v/v Alamar Blue indicator were added to each plate containing scaffolds, and the plates were incubated for 4 hours at 37° C. Absorbance of the extracted dye, which is proportional to the number of cells attached to the scaffold, was measured spectrophotometrically with a micro plate reader (Molecular Device, Versamax turnable microplate reader) at wavelengths of 570 and 600 nm. A calibration curve, generated from a known number of MG63 osteoblast-like cells reacting with the Alamar Blue indicator, was used to quantify the number of cells attached on scaffolds.

In Vivo Study: Skeletally mature female adult Sprague-Dawley rats (approximately 2 months old and weighing 200 g) were anesthetized with pentobarbital (35 mg/kg). After the skin was prepared and sterilized with iodine and ethanol, a 22-gauge spine needle was used to puncture the trochanteric area of the rat for bone marrow. A 2 cm incision was made on the lateral thigh of the rat. The quadrel femoral muscle was exposed and an incision of ~1.5 cm was cut on the muscle to make a small pouch. A cubic scaffold with dimensions of 4 mm×4 mm×4 mm and infused with bone marrow from the same rat was implanted into the muscle pouch. All rats were monitored for signs of infection. All surgical incisions healed without evidence of infection or other complications. The rats were euthanized with an over-dose of pentobarbitol (100 mg/kg) to harvest the implanted scaffolds in a group of three at 1, 2, 4, 8, and 12 weeks after surgery. The histological assessment was the same as the in vitro experiment, except that the harvested samples were immersed in 10% formaldehyde.

Strength and Porosity: Scaffolds for bone tissue engineering require a highly porous structure, wherein the pores are interconnected, to ensure a biological environment conducive to cell attachment and proliferation as well as tissue growth, in addition to permitting the passage of nutrients within the scaffold.

Scanning Electron Microscopy revealed that scaffolds of the present invention, made from 4.8 wt % chitosan-alginate, and scaffolds made from 4.8 wt % pure chitosan are both highly porous with a pore size around 100-300 μm, and wherein the pores are highly interconnected. This porous structure is favorable for cell attachment and new bone tissue ingrowth (Yang, S., et al., *Tissue Eng.* 7:679-89, 2001; Chu, T. M., et al., *Biomaterials* 23:1283-93, 2002; Zhang, Y. and Zhang, M., *J. Biomed. Mater. Res.* 55:304-12, 2001). Scaffolds for bone tissue engineering must have enough mechanical strength to support bone tissue regeneration at the site of implantation and maintain sufficient structural integrity during both in vitro and in vivo cell growth (Thomson, R. C., et al., *J. Biomater. Sci. Polym. Ed.* 7:23-38, 1995; Zhang, Y. and Zhang, M., *J. Biomed. Mater. Res.* 62:378-86, 2002; Sugimoto, M., et al., *Carbohydrate Polymers* 36:49-59, 1998). One of the major challenges in fabrication of porous scaffolds is the trade-off between adequate porosity and mechanical strength (Thomson, R. C., et al., *J. Biomater. Sci. Polym. Ed.* 7:23-38, 1995). The porosity of the scaffolds was evaluated with a liquid displacement method using ethanol as the displacing liquid (Whang, K., et al., *Tissue Eng.* 5:35-51, 1999; Wake, M. C., et al., *Cell Transplant* 3:339-43, 1994). The porosities of pure chitosan and chitosan-alginate scaffolds in this study were determined to be 84.86±2.18% and 91.94±0.90%, respectively. Compression tests of both chitosan and chitosan-alginate scaffolds were carried out to obtain the stress-strain relations from which the compressive yield strength and compressive modulus were calculated. The compressive yield strength and compressive modulus were determined to be 0.125±0.015 MPa and 2.56±0.41 MPa, respectively, for porous structures made from pure chitosan, and 0.46±0.022 MPa and 8.16±1.57 MPa, respectively, for porous structures made from chitosan-alginate in accordance with the present invention.

Without wishing to be bound by theory, the significant increase in compressive modulus and compressive yield strength for the chitosan-alginate scaffold could be attributed to the strong ionic interactions between chitosan and alginate. The strong ionic interactions between chitosan and alginate were confirmed by FTIR analysis. The characteristic peak of alginate was seen at 1620 cm$^{-1}$ corresponding to a carbonyl (C=O) bond. The chitosan spectrum showed characteristic bands of amide-I (1643 cm$^{-1}$), amide II (1574 cm$^{-1}$), and amino groups (1173 cm$^{-1}$). Chitosan used in these experiments was 85% deacetylated. The double amide peaks observed for chitosan corresponded to the partial N-deacetylation of chitin (Takahashi, T., et al., *Int. J. Phar.* 61:35-41, 1990). The peaks observed at 1424 cm$^{-1}$ and 1070 cm$^{-1}$ in both alginate and chitosan scaffolds corresponded to carboxyl —COOH and C—O stretching bands, respectively. In the chitosan-alginate spectrum, amide II peaks were significantly intensified, amide I peak was shifted from 1643 cm$^{-1}$ to 1654 cm$^{-1}$, and the peak for the amino group (1173 cm$^{-1}$) was absent. These changes suggest the formation of a chitosan-alginate complex as a result of the ionic interaction between the negatively charged carbonyl group (—COOH) of alginate and the positively charged amino group (—NH$_2$) of chitosan (Brine, C. J., Sanford, P. A., Zikakis, J. P., *Advances in Chitin and Chitosan* (ed. C. Mireles, Martino, M., Bouzas, J., Torres, J. A.) (Elsevier, London, 1992); Wang, L., et al., *J. Pharm. Sci.* 90:1134-42, 2001; Khalid, M. N., et al., *Eur. J. Pharm. Sci.* 15:425-32, 2002). An apparent change in spectrum was seen after chitosan-alginate was cross-linked with CaCl$_2$. The amide-I (C=O, 1643 cm$^{-1}$) and amide-II (C—N, 1574 cm$^{-1}$) bands were replaced by a new band (1620 cm$^{-1}$), as a result of the interaction of two residual carboxylic groups on alginate linking adjacent coacervates into a network matrix.

Shape retention: Swelling behavior and structural stability of scaffolds are critical for their practical use in tissue engineering. Most natural polymers, including chitosan, swell readily in biological fluids. Tissue culture studies, in vitro, indicated that initial swelling is desirable and the resultant increase in pore size facilitates cell attachment and growth in a three-dimensional fashion (Shanmugasundaram, N., et al., *Biomaterials* 22:1943-51, 2001). Continuous swelling would lead, however, to loss of mechanical integrity and production of compressive stress applied to surrounding tissue.

Swelling behavior of a scaffold depends strongly on the pH value at the site of implantation within a living body. The swelling properties of chitosan scaffolds, and chitosan-alginate scaffolds, were investigated in vitro by immersing the scaffolds for two weeks in a liquid (pH 7.4) that simulated a bodily fluid. After two weeks immersion in the liquid, the chitosan-alginate scaffold retained its overall size and cylindrical shape, while swelling of the chitosan scaffold was noted. The swelling behavior of the chitosan scaffolds differed distinctly in the three solutions of different pH. The chitosan scaffold in 1N HCl started to swell rapidly and the scaffold dissolved in two hours. The chitosan scaffold in SBF solution (pH=7.4) also swelled over time, with its diameter increasing by ~20% within two hours, but then underwent a minor swelling thereafter at a significantly reduced rate. The chitosan scaffold in 1N NaOH basic solution (pH=14) swelled initially (<5%) but retained its overall size thereafter for weeks. The chitosan scaffold was stable only in solutions of physiological or higher pH.

In contrast to the chitosan scaffolds, the swelling behavior of the chitosan-alginate scaffolds was about the same in all three solutions: except an initial swelling (within a half hour), the scaffolds retained their overall size through the period of study (6 weeks). These observations suggest that chitosan-alginate scaffolds are stable regardless of the pH value of solution. This stability across a range of pH values makes the chitosan-alginate scaffold potentially applicable to a wide range of clinical applications. Without wishing to be bound by theory, swelling and degradation of pure chitosan is likely caused, at least in part, by the protonation of amino/imine groups on the surface of the material, and the mechanical relaxation of coiled chitosan chains (Vachoud, L., et al., *Carbohydr. Res.* 326:295-304, 2000; Aiba, S., *Int. J. Biol. Macromol.* 13:40-4, 1991; Montanaro, L., et al., *Biomaterials* 23:3651-9, 2002). Again without wishing to be bound by theory, the stability of chitosan-alginate scaffolds is likely caused, at least in part, by (1) the interaction of amine groups on chitosan with carboxyl groups on alginate which prevents the protonation of amino groups on chitosan, and (2) the presence of carboxyl groups on alginate that buffers the solution and slows chitosan degradation.

Figure 3:
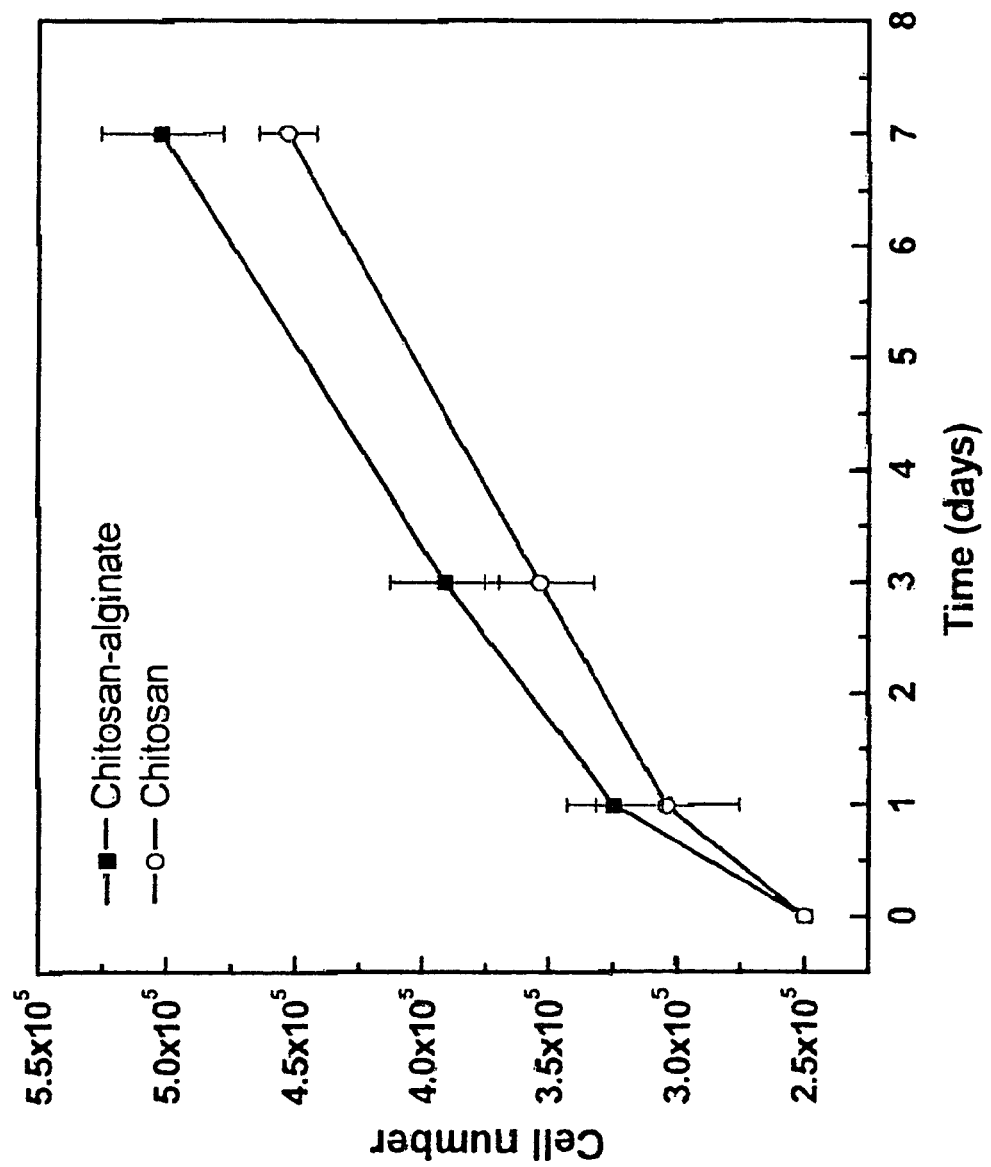
FIG. 3 shows the number of osteoblasts attached to a chitosan scaffold and to a chitosan-alginate scaffold after 1, 3 and 7 days of cell culture.

Osteoblast Integration and Function: Cell attachment, proliferation, and differentiation on a material, over time, demonstrate the cellular compatibility of the material, and provide an indication of the suitability of the material for tissue engineering applications. Osteoblast proliferation on both chitosan and chitosan-alginate scaffolds was assessed using an Alamar Blue assay. FIG. 3 shows the number of cells attached to chitosan and chitosan-alginate scaffolds after 1, 3 and 7 days of cell culture. The number of cells on both chitosan and chitosan-alginate scaffolds increased with time. More cells were observed on the chitosan-alginate scaffolds than on pure chitosan scaffolds throughout the period of study.

Scanning electron microscopy (SEM) was used to study the osteoblasts that grew on the chitosan and chitosan-alginate scaffolds after 3 days and 7 days of culture. At day 3, osteoblast cells on the chitosan scaffold showed an elongated shape and were anchored to the surface by discrete filopodia. More cells were seen on the chitosan-alginate scaffold than on the chitosan scaffold throughout the period of study. A number of microvilli appeared on the dorsal surfaces of cells. The majority of cells on the both scaffolds gathered together and formed clusters while the others randomly attached on the material surface. The surface of the cells on the chitosan appeared to be smoother than those on the chitosan-alginate scaffold. Most notably, cell morphology on the chitosan-alginate scaffold differed distinctly than on the chitosan scaffold in that a layer of small particles covered the cells grown on the chitosan-alginate scaffold. These particles are calcium rich minerals as identified by energy dispersive spectroscopy (EDS) as discussed below.

Formation of calcium phosphate salts, or mineral deposition, is a primary function of osteoblast cells (Lu, H. H., et al., *J. Biomed. Mater. Res.* 64A:465-74, 2003). Surface chemical compositions of cells on scaffolds and on extracellular matrices were determined by EDS. The EDS spectra were taken from the cell surfaces as well as the scaffold matrices. The EDS cell surface spectra of osteoblasts on the chitosan scaffold showed no sign of phosphate or calcium after 7 days of culture. In contrast, the EDS cell surface spectra of osteoblasts cultured on the chitosan-alginate scaffold showed both calcium and phosphate signals, and their amounts increased from day 3 to day 7. These results suggest that both the individual cells and cell clusters on the chitosan-alginate scaffold contributed to the production of calcium and phosphate.

Mineral deposition in large areas was confirmed by Von Kossa assay (Sheehan, D., H. B. *Theory and Practice of Histotechnology*, 2d ed. (Battelle Press, Ohio, 1980)) on chitosan-alginate scaffolds after culture both in vitro and harvested in vivo at 4 and 8 weeks after implantation. In in vitro studies, calcium appeared scattered around the cell clusters on the both chitosan and chitosan-alginate scaffolds at day 10, and more calcium was seen at day 28, and some of it had gathered to form chunks. The mineralization increased with cell culture time, in agreement with the results from the EDS analysis described above. In in vivo studies, calcium was seen on the composite scaffold at week 4. The scaffolds harvested at week 8 showed more calcium carbonate deposits of different sizes. The presence of calcium and phosphate, and the observation that their amounts increased over time, indicated that the chitosan-alginate scaffold promoted bone cell growth and mineral deposition (Boskey, A. L., *Clin. Orthop.*, 244-74, 1992). The amount of calcium carbonates formed in the in vivo study seemed less than that in the in vitro study. This might be due to the fact that only MG63 cells were used in the in vitro study which were capable of producing minerals, while only a small number of MG63 cells were present in bone marrow for the in vivo study.

In Vivo Tissue Compatibility: Tissue compatibility of chitosan-alginate scaffolds infused with bone marrow was assessed in vivo by implanting them into muscles of rats and harvesting after 1, 2, 4, 8, and 12 weeks of implantation. All surgical incisions healed without evidence of infection or other complications. At harvest, the scaffolds were stained with HE and Masson's trichrome.

After 1 and 2 weeks of implantation, neutrophils migrated from blood into the scaffolds, but subsided quickly over time from week 1 to week 2. The formation of blood sinus was clearly seen at week 2. There was no visible evidence of fibrosis, at week 12, between the scaffold and surrounding muscle, which is in contrast to most synthetic polymers where fibrotic layers are usually formed due to the adverse foreign body reaction caused by acidic degradation products (Lutolf, M. P., et al., *Nat. Biotechnol.* 21:513-8, 2003).

Masson's trichrome was used to stain the harvested scaffolds to visualize the formation of collagen and vascularization. Collagen appeared 4 weeks after implantation and increased quickly over time; at week 12 collagen was deposited throughout the entire scaffold indicating that the cells had fully penetrated into the scaffold. A vascularized environment is necessary for the construction of a large volume of tissue. At week 4 a large number of small blood vessels were seen in the scaffold and the size of the blood vessels increased over time from week 4 to week 12. The highly angiogenic response of the host to the implanted construct ensured sufficient nutrient in the scaffold and allowed cells to survive and proliferate after extended periods. At week 12, the scaffolds completely degraded and the new tissue integrated well with adjacent muscles.

EXAMPLE 2

This Example describes a method for measuring the compressive modulus and compressive yield strength of porous structures of the present invention.

A circular disc, prepared as described herein from chitosan and alginate, having uniform cross section, A, is measured in compression by applying loads at the ends that are distributed evenly over the gage of the specimen. The stress, $\sigma$, is calculated using the force applied, F, as $$\sigma = \frac{F}{A} \qquad (1)$$

Strain, $\epsilon$, the normalized deformation is given by $$\varepsilon = \frac{l_f - l_0}{l_0} \qquad (2)$$

where, $l_f$ is the final length after testing and $l_o$ is the initial length of the material.

The compressive yield strength was determined from the intersection of the two tangents on the stress-strain curve around the yield point.

The compressive modulus, E, of the material is the intrinsic property that is calculated from the slope of the linear portion of the stress strain curve, and is given by $$E = \frac{\sigma}{\varepsilon} \qquad (3)$$

An Instron 4505 mechanical tester with 10 kN load cells is used for the compression test. The specimens to be tested are circular discs of 13 mm in diameter and 12 mm in thickness. The crosshead speed is set at 0.4 mm/min, and the load is applied until the specimen cracks. Compressive yield strength and compressive modulus are calculated using Equations 1-3 set forth in this Example. Five samples of each type are tested for mechanical properties, and the results are averaged.

EXAMPLE 3

This Example describes a method for measuring the density and porosity of a porous structure of the present invention. This method was used to determine the density and porosity of the porous structures described in the Examples of the present patent application.

The density and porosity of porous structures are determined using a liquid displacement method. A sample of weight W is placed in a graduated cylinder containing a known volume ($V_1$) of ethanol. The sample is kept in the ethanol for 5 minutes, and a series of brief evacuation-repressurization cycles is conducted to force air out the pores of the structure. The cycling is continued until no air bubbles emerge from the structure. The total volume of ethanol and the ethanol-impregnated scaffold are recorded as $V_2$. The volume difference ($V_2-V_1$) is the volume of the skeleton of the structure. The ethanol-impregnated structures are removed from the cylinder, and the residual ethanol volume is recorded as $V_3$. The total volume of the structure is $V=(V_2-V_1)+(V_1-V_3)=V_2-V_3$. The density of the scaffold is expressed as $d=W/(V_2-V_3)$, and the porosity ($\rho$) of the scaffold is given by $\rho=(V_1-V_3)/(V_2-V_3)$.

EXAMPLE 4

This Example describes a method for measuring the average diameter of pores in a porous structure of the present invention.

A portion of a porous structure is coated with gold/palladium under an argon atmosphere. A JEOL 5200 scanning electron microscope is used to produce an image of the coated portion of the porous structure. The diameter of each pore within a square area of the image is measured. All of the diameter values are added together and divided by the number of pores that were measured. The resulting value is the average pore diameter.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for growing living cells in a porous structure, the method comprising the step of growing living cells in pores defined by a porous structure comprising chitosan, alginate, and divalent metal cations, wherein
   (a) the porous structure comprises chitosan that is ionically linked to alginate; and
   (b) the structure has a compressive yield strength of at least 0.35 MPa.

2. A method of claim 1 wherein the living cells are osteoblasts.

3. A method of claim 1 wherein the structure is biodegradable.

4. A method of claim 1 wherein the living cells are bone-forming cells.

5. A method of claim 1 further comprising a biologically active molecule selected from the group consisting of an antibiotic and a protein that promotes the growth of bone-forming cells.

6. A method of claim 1 wherein the ratio of chitosan to alginate is from 1:1 to 4:1.

7. A method of claim 1 wherein the divalent metal cations are selected from the group consisting of $Ca^{2+}$, $Ba^{2+}$, $Mg^{2+}$, and $Sr^{2+}$.

8. A method of claim 1 wherein the divalent metal cations are $Ca^{2+}$ ions.

9. A method of claim 1 wherein the porous structure has a porosity of from 88% to 96%.

10. A method of claim 1 wherein the porous structure has a compressive modulus of from 5 MPa to 8 MPa.

* * * * *

UNITED STATES PATENT AND TRADEMARK OFFICE
CERTIFICATE OF CORRECTION

PATENT NO.         : 7,736,669 B2                                           Page 1 of 1
APPLICATION NO.    : 11/002996
DATED              : June 15, 2010
INVENTOR(S)        : M. Zhang et al.

It is certified that error appears in the above-identified patent and that said Letters Patent is hereby corrected as shown below:

| COLUMN | LINE | ERROR |
|--------|------|-------|
| 1 | 7-11 | "The U.S. Government has a paid-up license in this invention and the right in limited circumstances to require the patent owner to license others on reasonable terms as provided for by the terms of grant NSF-EEC 9529161 awarded by the National Science Foundation." |
|   |      | should read |
|   |      | --This invention was made with government support under NSF-EEC 9529161 awarded by the National Science Foundation. The government has certain rights in the invention.-- |

Signed and Sealed this
Thirty-first Day of January, 2012

David J. Kappos
*Director of the United States Patent and Trademark Office*